United States Patent
Ding et al.

(10) Patent No.: US 10,709,699 B2
(45) Date of Patent: Jul. 14, 2020

(54) PYRIDONE DERIVATIVE PHARMACEUTICAL COMPOSITION AND PREPARATION METHOD THEREOF

(71) Applicant: Jiangsu Hengrui Medicine Co., Ltd., Lianyungang, Jiangsu (CN)

(72) Inventors: Huan Ding, Jiangsu (CN); Daimei Zhang, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 16/462,317

(22) PCT Filed: Nov. 24, 2017

(86) PCT No.: PCT/CN2017/112829
§ 371 (c)(1),
(2) Date: May 20, 2019

(87) PCT Pub. No.: WO2018/095403
PCT Pub. Date: May 31, 2018

(65) Prior Publication Data
US 2019/0314349 A1    Oct. 17, 2019

(30) Foreign Application Priority Data
Nov. 25, 2016    (CN) .......................... 2016 1 1053170

(51) Int. Cl.
*A61K 31/444* (2006.01)
*A61K 9/20* (2006.01)
*A61K 9/48* (2006.01)

(52) U.S. Cl.
CPC .......... *A61K 31/444* (2013.01); *A61K 9/2018* (2013.01); *A61K 9/2054* (2013.01);
(Continued)

(58) Field of Classification Search
CPC ...... A61K 31/444; A61K 31/519; A61K 9/20; A61K 9/2018; A61K 9/2054; A61K 9/2095; A61K 9/48; A61K 9/4858; A61K 9/4866

See application file for complete search history.

(56) References Cited

U.S. PATENT DOCUMENTS

2016/0244410 A1*    8/2016    Tu ........................ C07D 213/82

FOREIGN PATENT DOCUMENTS

| CN | 103998041 A | 8/2014 |
| CN | 104902876 A | 9/2015 |

(Continued)

OTHER PUBLICATIONS

Remington, the science and practice of pharmacy (19th edition, 1995) pp. 1682-1685 and pp. 1448-1523) (Year: 1995).*

(Continued)

*Primary Examiner* — Savitha M Rao
(74) *Attorney, Agent, or Firm* — Ice Miller LLP

(57) ABSTRACT

Provided are a pyridone derivative pharmaceutical composition and a preparation method thereof. In particular, provided are a pharmaceutical composition containing a pyridone derivative or a pharmaceutically acceptable salt thereof and the preparation method thereof. The pharmaceutical composition contains an active ingredient 2-((2-fluoro-4-iodophenyl)amino)-1-methyl-4-((6-methylpyridin-3-yl)oxy)-6-oxo-1,6-di hydropyridine-3-carboxamide or a pharmaceutically acceptable salt thereof, and hydroxypropyl methylcellulose, and the pharmaceutical composition has good dissolution.

17 Claims, 2 Drawing Sheets

(52) U.S. Cl.
CPC .......... *A61K 9/2095* (2013.01); *A61K 9/4858* (2013.01); *A61K 9/4866* (2013.01)

(56) References Cited

FOREIGN PATENT DOCUMENTS

| CN | 104936945 A | 9/2015 |
|---|---|---|
| WO | 2015058589 A1 | 4/2015 |
| WO | 2016155473 A1 | 10/2016 |

OTHER PUBLICATIONS

Int'l Search Report dated Feb. 26, 2018 in Int'l Application No. PCT/CN2017/112829.
The second method (paddle method) of the dissolution rate test described in general rule 0931 of vol. IV of Chinese Pharmacopoeia 2015 Edition.

\* cited by examiner

PYRIDONE DERIVATIVE PHARMACEUTICAL COMPOSITION AND PREPARATION METHOD THEREOF

CROSS-REFERENCE TO RELATED APPLICATION

This application is a Section 371 of International Application No. PCT/CN2017/112829, filed Nov. 24, 2017, which was published in the Chinese language on May 31, 2018, under International Publication No. WO 2018/095403 A1, which claims priority under 35 U.S.C. § 119(b) to Chinese Patent Application No. 201611053170.1, filed on Nov. 25, 2016, the disclosures of which are incorporated herein by reference in their entireties.

FIELD OF THE INVENTION

The present invention belongs to the field of pharmaceutical formulations, and specifically relates to a pharmaceutical composition comprising 2-((2-fluoro-4-iodophenyl)amino)-1-methyl-4-((6-methylpyridin-3-yl)oxy)-6-oxo-1,6-di hydropyridine-3-carboxamide or a pharmaceutically acceptable salt thereof and a method for preparing the same.

BACKGROUND OF THE INVENTION

Melanoma is the most aggressive type of skin cancer, and is the leading cause of death among skin diseases. According to the estimate of the National Cancer Institute of USA, in 2013, 76,690 Americans will be diagnosed with melanoma, while 9,480 people will die from this disease. About half of melanoma patients carry a mutated BRAF protein kinase gene. This abnormal mutation can promote the growth and spread of melanoma, and V600 accounts for the majority. Unfortunately, the chemotherapy using cytotoxin dacarbazine was the main treatment for malignant melanoma before 2011. Dacarbazine is a DNA alkylation drug that not only has a significant side effect, but also has a response rate of only about 10%, and the 1-year survival rate is only about 36%. In 2011, the launch of two breakthrough new drugs, Yervoy and Zelboraf, changed the status of melanoma treatment. On May 29, 2013, the USA Food and Drug Administration (FDA) approved a new drug Mekinist (trametinib) developed by GlaxoSmithKline (GSK) for the treatment of advanced or unresectable melanoma. Mekinist, as a single-drug oral tablet, is the first MEK inhibitor, and is suitable for the treatment of adult patients suffering from unresectable melanoma or metastatic melanoma carrying BRAF V600E or V600K mutation. The BRAF V600E mutation accounts for about 85% of all BRAF V600 mutations in metastatic melanoma, and the V600K mutation accounts for about 10% of all BRAF V600 mutations in metastatic melanoma. In a Mekinist trial of 322 patients, the survival was extended by 3.3 months in patients receiving Mekinist treatment compared with patients receiving chemotherapy.

CN103998041A discloses an oral solid formulation of the MEK inhibitor trametinib. The excipients used in this solid formulation are substantially free of water, so as to solve the problems of the stability, the dissolution rate of the solid formulation, and the adverse pharmacodynamics caused by the desolvation of the trametinib solvate when administered in vivo.

CN104902876A discloses a powder formulation comprising trametinib and a solubilizing agent, and the solubilizing agent is selected from cyclodextrin-based pharmaceutical auxiliary materials, so as to solve the problems of the dissolution rate of the powder formulation and the desolvation of the trametinib solvate when administered in vivo.

WO2015058589 discloses and is directed to 2-((2-fluoro-4-iodophenyl)amino)-1-methyl-4-((6-methylpyridin-3-yl)oxy)-6-oxo-1,6-di hydropyridine-3-carboxamide or a pharmaceutically acceptable salt thereof, which is useful as an inhibitor of MEK activity, especially in the treatment of cancer. WO2016155473 discloses the crystal form I of 2-((2-fluoro-4-iodophenyl)amino)-1-methyl-4-((6-methylpyridin-3-yl)oxy)-6-oxo-1,6-di hydropyridine-3-carboxamide p-toluenesulfonate (compound A) and a method for preparing the same.

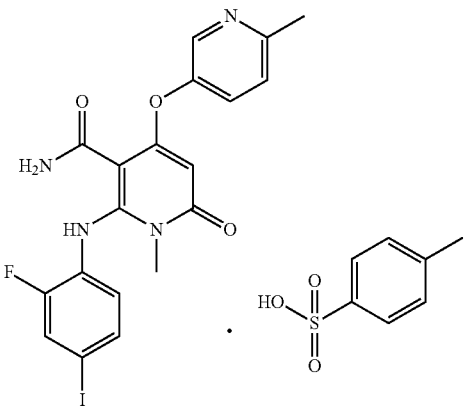

Forms of a pharmaceutically active compound having low solubility may encounter a number of challenges in the preparation of a high quality solid pharmaceutical composition or solid formulation (such as tablets, granules, and micro-powder). The solubility of compound A and its salts is low, and none of the above documents mentions how to solve such problems so as to provide a composition having a satisfactory dissolution rate.

SUMMARY OF THE INVENTION

The present invention provides an oral solid pharmaceutical composition, comprising an active ingredient 2-((2-fluoro-4-iodophenyl)amino)-1-methyl-4-((6-methylpyridin-3-yl)oxy)-6-oxo-1,6-di hydropyridine-3-carboxamide or a pharmaceutically acceptable salt thereof, and hydroxypropyl methylcellulose. This pharmaceutical composition has improved properties of rapid dissolution, good stability and acceptable dissolution rate and disintegration rate, which contribute to guaranteed safe and effective medication. Moreover, the preparation process of the pharmaceutical composition is simple, and more suitable for industrial production.

In an embodiment of the present invention, the active ingredient can be present in an amount of 0.01-10%, preferably 0.1-5%, and of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.9, 3.0, 3.1, 3.2, 3.3, 3.4, 3.5, 3.7, 3.9, 4.1, 4.3, 4.5, 4.7, 4.9 or 5.0% by weight, relative to the weight of the pharmaceutical composition.

Further, the weight of the active ingredient of the present invention 2-((2-fluoro-4-iodophenyl)amino)-1-methyl-4-((6-methylpyridin-3-yl)oxy)-6-oxo-1,6-di hydropyridine-3-carboxamide in the oral solid pharmaceutical composition is 0.125 mg, 0.5 mg, 1 mg or 2 mg; or the weight of the pharmaceutically acceptable salt (for example p-toluenesulfonate) of the active ingredient of the present invention in the pharmaceutical composition is 0.168 mg, 0.674 mg, 1.348 mg or 2.694 mg, relative to 100 mg of the oral solid pharmaceutical composition per unit (100 mg/unit).

Further, the hydroxypropyl methylcellulose of the present invention is present in an amount of 0.5-10%, preferably 1-5%, relative to the weight of the pharmaceutical composition, and of 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9 or 5.0%, and more preferably 1.5-3% by weight, relative to the weight of the pharmaceutical composition.

Further, the weight of the hydroxypropyl methylcellulose of the present invention in the oral solid pharmaceutical composition is 2.0 mg, 2.1 mg, 2.2 mg, 2.3 mg, 2.4 mg, 2.5 mg, 2.6 mg, 2.7 mg, 2.8 mg, 2.9 mg or 3.0 mg, relative to 100 mg of the oral solid pharmaceutical composition per unit (100 mg/unit).

In order to ensure that the pharmaceutical composition has a good dissolution property, the active ingredient in the pharmaceutical composition of the present invention needs to be micronized before the preparation, so as to obtain the desired particle size. In an embodiment, the particle size of 90% of the active ingredient particles (which can be expressed as D90 or d (0.9)) is less than or equal to 50 μm, and can be 50, 45, 40, 35, 30, 25, 20, 15, 10, 9, 8, 7, 6, 5, 4, 3, 2 or 1, and preferably less than or equal to 10 μm.

The pharmaceutical composition of the present invention can also comprise at least one pharmaceutical auxiliary material selected from the group consisting of a filler, a disintegrant, a glidant, a lubricant and a coating agent.

The term "relative to the weight of the pharmaceutical composition" of the present invention means that the calculation of usage amount ranges of the active ingredient or other kinds of pharmaceutical auxiliary materials is based on the weight of tablet core without coating agent, see Example 1 for details.

The filler provides volume to formulate a tablet with a practical size that can be processed. The filler can also contribute to the process, and improve the physical properties of the pharmaceutical composition such as fluidity, compressibility and hardness of solid formulation. The interaction of the filler with the active ingredient is of particular interest to those skilled in the art, since the amount of filler used in the pharmaceutical composition is large, and the filler is in direct contact with the active ingredient (or active compound). The filler of the present invention is known or determinable by those skilled in the art, and may preferably be, but not limited to, at least one of mannitol, lactose, microcrystalline cellulose, pregelatinized starch and calcium hydrophosphate. The filler of the present invention is present in an amount of 30-95%, preferably 50-94%, relative to the weight of the pharmaceutical composition, and of 50, 52, 54, 56, 58, 60, 62, 64, 66, 68, 70, 72, 76, 80, 82, 86, 88, 89, 90, 91, 92, 93 or 94% by weight, relative to the weight of the pharmaceutical composition.

Further, the weight of the filler of the present invention in the oral solid pharmaceutical composition is 80 mg, 81 mg, 82 mg, 83 mg, 84 mg, 85 mg, 86 mg, 87 mg, 88 mg, 89 mg, 90 mg, 91 mg, 92 mg, 93 mg or 94 mg, relative to 100 mg of the oral solid pharmaceutical composition per unit (100 mg/unit).

In an embodiment of the present invention, the filler is preferably at least one selected from the group consisting of mannitol and microcrystalline cellulose; further, the pharmaceutical composition of the present invention uses mannitol and microcrystalline cellulose as the filler, wherein the weight ratio of mannitol to microcrystalline cellulose is 1.5:1-10:1. In order to further improve the punch jamming phenomenon during the preparation of tablets, the weight ratio of mannitol to microcrystalline cellulose is 1.8:1-4:1, and can be 1.9:1, 2:1, 2.2:1, 2.4:1, 2.6:1, 2.8:1, 3:1, 3.2:1, 3.4:1, 3.6:1, 3.8:1 or 4:1.

The disintegrant is used to promote disruption or disintegration of the pharmaceutical composition after administration. The disintegrant of the present invention is known or determinable by those skilled in the art, and can be, but is not limited to, starch, cellulose, gum, cross-linked polymer and foaming agent, for example, corn starch, potato starch, pregelatinized starch, modified corn starch, croscarmellose sodium, crospovidone, sodium starch glycolate, magnesium aluminum silicate HV, methylcellulose, microcrystalline cellulose, cellulose, colloidal silicon dioxide, natural sponge, cation exchange resin, and preferably at least one selected from the group consisting of croscarmellose sodium, sodium carboxymethyl starch, crospovidone, low-substituted hydroxypropyl cellulose, croscarmellose sodium, sodium carboxymethyl starch, crospovidone and low-substituted hydroxypropyl cellulose. Further, the disintegrant of the present invention is present in an amount of 2-15%, relative to the weight of the pharmaceutical composition, and of 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15% by weight, relative to the weight of the pharmaceutical composition.

The lubricant is usually used to facilitate processing, prevent the formulation materials from adhering to the production equipment, reduce the friction between particles, improve the flow rate of the formulation, and help the formulation to be discharged from the production equipment. The lubricant of the present invention is known or determinable by those skilled in the art, and can be, but is not limited to, talc, stearate (such as magnesium stearate, calcium stearate and zinc stearate), polyethylene glycol, ethylene oxide polymer, liquid paraffin, lauryl sodium phosphate, leucine, sodium stearyl fumarate, and preferably at least one selected from the group consisting of magnesium stearate, stearic acid, palmitic acid, calcium stearate, talc, carnauba wax and sodium stearyl fumarate. Further, the lubricant of the present invention is present in an amount of 0.1-5%, relative to the total weight of the pharmaceutical composition, and of 0.1, 0.2, 0.3, 0.4, 0.5, 0.6, 0.7, 0.8, 0.9, 1, 1.2, 1.4, 1.6, 1.8, 2, 2.2, 2.4, 2.6, 2.8, 3.0, 3.2, 3.4, 3.6, 3.8, 4, 4.2, 4.4, 4.6, 4.8 or 5%, and preferably 0.5-3% by weight, relative to the total weight of the pharmaceutical composition.

An embodiment of the present invention provides a pharmaceutical composition comprising:
a) 0.1-5% by weight of 2-((2-fluoro-4-iodophenyl)amino)-1-methyl-4-((6-methylpyridin-3-yl)oxy)-6-oxo-1,6-di hydropyridine-3-carboxamide or a pharmaceutically acceptable salt thereof,
b) 2-15% by weight of a disintegrant,
c) 50-94% by weight of a filler,
d) 1.5-3% by weight of hydroxypropyl methylcellulose,
e) optionally 0.5-3% by weight of a lubricant,
wherein, the filler is preferably at least one selected from the group consisting of mannitol and microcrystalline cellulose; the disintegrant is at least one selected from the group consisting of croscarmellose sodium, sodium carboxymethyl starch, crospovidone and low-substituted hydroxypropyl cellulose; and the lubricant is at least one selected from the group consisting of magnesium stearate, stearic acid, palmitic acid, calcium stearate, talc, carnauba wax and sodium stearyl fumarate.

Further, the filler is obtained by mixing mannitol with microcrystalline cellulose, the weight ratio of the two pharmaceutical auxiliary materials is 1.5:1-10:1, and preferably 1.8:1-4:1.

In a specific embodiment, the pharmaceutical composition of the present invention can also comprise a coating agent. The coating agent (a non-site-specific release coating) can be, but is not limited to, hydroxypropyl methylcellulose, methylcellulose, ethylcellulose, methylcellulose or hydroxypropyl cellulose, polyvinyl alcohol, povidone, polyvinyl acetate resin or polyvinyl acetal diethylaminoacetate, aminoalkyl methacrylate copolymer RS and ethyl acrylate-methyl methacrylate copolymer dispersion, saccharides including sugar alcohol, sucrose, mannitol paste, or Opadry (trade name), and preferably Opadry.

The present invention also provides a method for preparing the pharmaceutical composition of the present invention, comprising the steps of: 1) mixing 2-((2-fluoro-4-iodophenyl)amino)-1-methyl-4-((6-methylpyridin-3-yl)oxy)-6-oxo-1,6-dihydropyridine-3-carboxamide or a pharmaceutically acceptable salt thereof with a disintegrant and optionally at least one pharmaceutical auxiliary material selected from the group consisting of a filler, a binder, a lubricant and a glidant, 2) granulating the mixture obtained in step 1) followed by tableting the resulting granules or filling them into capsules, or directly tableting the mixture obtained in step 1), or directly filling the mixture obtained in step 1) into capsules; further, the granulation step is followed by a coating step, the coating agent is Opadry, hydroxypropyl methylcellulose, ethylcellulose or polyvinyl alcohol, and preferably Opadry.

The granulation method used in the present invention can be wet granulation or dry granulation. When the wet granulation method is used, fluidized bed granulation or high speed shear wet granulation can be employed.

In a specific embodiment of the present invention, the steps for high speed shear granulation process are as follows:

1) mixing 2-((2-fluoro-4-iodophenyl)amino)-1-methyl-4-((6-methylpyridin-3-yl)oxy)-6-oxo-1,6-di hydropyridine-3-carboxamide or a pharmaceutically acceptable salt thereof with a filler and a disintegrant, 2) adding a solution comprising hydroxypropyl methylcellulose to the mixture of step 1) to prepare a soft material, then wet-milling the soft material, followed by drying and milling it, 3) adding a lubricant to the granules obtained in step 2) and mixing them, 4) compressing the mixture obtained in step 3) into tablets.

In a specific embodiment of the present invention, the steps for fluidized bed granulation process are as follows:

1) mixing 2-((2-fluoro-4-iodophenyl)amino)-1-methyl-4-((6-methylpyridin-3-yl)oxy)-6-oxo-1,6-di hydropyridine-3-carboxamide or a pharmaceutically acceptable salt thereof with a filler and a disintegrant, 2) fluidizing the powder mixture obtained in step 1), then spraying a solution comprising hydroxypropyl methylcellulose to the surface of the powder mixture, followed by drying and milling them, 3) adding a lubricant to the granules obtained in step 2) and mixing them, 4) compressing the mixture obtained in step 3) into tablets.

In a preferred embodiment of the present invention, the granulation method adopts high speed shear granulation or fluidized bed granulation.

The present invention also provides an oral solid pharmaceutical composition, comprising an active ingredient 2-((2-fluoro-4-iodophenyl)amino)-1-methyl-4-((6-methylpyridin-3-yl)oxy)-6-oxo-1,6-di hydropyridine-3-carboxamide or a pharmaceutically acceptable salt thereof, mannitol and microcrystalline cellulose, wherein the weight ratio of mannitol to microcrystalline cellulose is 1.5:1-10:1, which can greatly improve the pharmaceutical composition; further, the weight ratio of mannitol to microcrystalline cellulose is 1.8:1-4:1, and can be 1.9:1, 2:1, 2.2:1, 2.4:1, 2.6:1, 2.8:1, 3:1, 3.2:1, 3.4:1, 3.6:1, 3.8:1 or 4:1; moreover, in the oral solid pharmaceutical composition of the present invention, mannitol and microcrystalline cellulose are present in a total amount of 30-95%, preferably 50-94%, and of 50, 52, 54, 56, 58, 60, 62, 64, 66, 68, 70, 72, 76, 80, 82, 86, 88, 89, 90, 91, 92, 93 or 94% by weight, relative to the weight of the pharmaceutical composition.

Further, the weight of the filler of the present invention in the oral solid pharmaceutical composition is 80 mg, 81 mg, 82 mg, 83 mg, 84 mg, 85 mg, 86 mg, 87 mg, 88 mg, 89 mg, 90 mg, 91 mg, 92 mg, 93 mg or 94 mg, relative to 100 mg of the oral solid pharmaceutical composition per unit (100 mg/unit).

The oral solid pharmaceutical composition (solid formulation) of the present invention can be a tablet, a granule, a powder (including a fine granule), or a capsule. The solid formulation can be obtained by widely known preparation methods. The maximum water content of the final dry granules after granulation is controlled below 3%, and then the granules are filled into capsules or directly packaged as a granule. When the dosage form is a tablet, the humidity of the tableting environment is controlled during the tableting process to ensure that the water content of the final raw tablets is less than 3% (below 3%). The final composition is treated by a vacuum drying method to ensure that the water content of the final composition is less than 3%.

When the pharmaceutical composition of the present invention is a tablet, the tablet can be prepared by compressing the granules obtained as described above. The pressure of compression can be determined within an appropriate range, and the pressure is preferably 1-10 kN. Moreover, the shape of the tablet is not particularly limited, and is preferably lenticular, discal, circular, oval (such as a caplet), teardrop or polygonal (such as triangle or rhombic). The prepared tablets can be coated by spraying a suspension/solution of the coating agent through a pan coater. After the coating is completed, the water content of the final tablet is controlled to be within 3% by a drying process. The drying temperature can be 40-80° C., and preferably 50-60° C. The drying method can be carried out by ordinary oven drying or vacuum drying.

When the pharmaceutical composition of the present invention is a granule, the granules obtained as described above can be used directly, or granulated into the desired granules by suitable techniques. Moreover, the granules thus prepared can be coated with a coating agent by spraying a suspension/solution of the coating agent.

The pharmaceutically acceptable salt of 2-((2-fluoro-4-iodophenyl)amino)-1-methyl-4-((6-methylpyridin-3-yl)oxy)-6-oxo-1,6-di hydropyridine-3-carboxamide of the present invention is a p-toluenesulfonate.

The dissolution rate of the pharmaceutical composition of the present invention is determined according to the second method (paddle method) of the dissolution rate test described in general rule 0931 of volume IV of Chinese Pharmacopoeia 2015 Edition. The dissolution test of the composition of the present invention is carried out using pH 6.8 phosphate buffer, preferably 1000 ml of pH 6.8 phosphate buffer as a dissolution medium at 37±0.5° C. and at the paddle speed of 50 rpm. The dissolution rate in 45 minutes is greater than or equal to 90%, and can be greater than or equal to 90%, 91%, 92%, 93%, 94%, 95%, 96%, 97%, 98%, 99% or 100%, and is preferably greater than or equal to 94%.

Further, the dissolution rate in 30 minutes is greater than or equal to 80%, and can be greater than or equal to 80%, 81%, 82%, 83%, 84%, 85%, 86%, 87%, 88%, 89%, 90%, 91%, 92%, 93%, 94%, 95%, 96%, 97%, 98%, 99% or 100%, and is preferably greater than or equal to 85%.

The 2-((2-fluoro-4-iodophenyl)amino)-1-methyl-4-((6-methylpyridin-3-yl)oxy)-6-oxo-1,6-di hydropyridine-3-carboxamide of the present invention can be obtained by the methods described in WO2015058589 and WO2016155473. The pharmaceutical auxiliary materials used in the present invention, such as lactose, microcrystalline cellulose and the like, are all commercially available.

DETAILED DESCRIPTION OF THE INVENTION

The present invention is further described in detail by the following examples and experimental examples. These examples and experimental examples are for illustrative purposes only, and are not intended to limit the scope of the present invention.

Example 1

According to the ratios shown in Table 1, 2-((2-fluoro-4-iodophenyl)amino)-1-methyl-4-((6-methylpyridin-3-yl)oxy)-6-oxo-1,6-di hydropyridine-3-carboxamide p-toluenesulfonate (hereinafter referred to as compound A), mannitol, microcrystalline cellulose and croscarmellose sodium were wet-granulated by a high speed shear granulator, using a 5% aqueous solution of povidone K30 or a 3% or 4% aqueous solution of hydroxypropyl methylcellulose as a wetting agent. The wet and soft material was wet-milled and dried, and then the dry granules (water content less than 3%) were dry-milled. A prescription amount of magnesium stearate was added, and mixed well with the granules. The resulting total mixed granules were compressed into tablets.

TABLE 1

| Ingredient | Experimental examples (mg/tablet) | | | |
|---|---|---|---|---|
| | 1 | 2 | 3 | 4 |
| Compound A | 2.7 | 2.7 | 2.7 | 2.7 |
| Mannitol | 70 | 70 | 60 | 59 |
| Microcrystalline cellulose pH101 | 20 | 20 | 30 | 30 |
| Croscarmellose sodium | 5 | 5 | 5 | 5 |

TABLE 1-continued

| Ingredient | Experimental examples (mg/tablet) | | | |
|---|---|---|---|---|
| | 1 | 2 | 3 | 4 |
| Povidone K30 (5%) | 3 | — | — | — |
| Hydroxypropyl methylcellulose E5 (3%) | — | 1.7 | 2 | — |
| Hydroxypropyl methylcellulose E5 (4%) | — | — | — | 2.4 |
| Magnesium stearate | 1.0 | 1.0 | 1.0 | 1.0 |
| Total | 101.7 | 100.4 | 100.7 | 100.1 |

Figure 1:
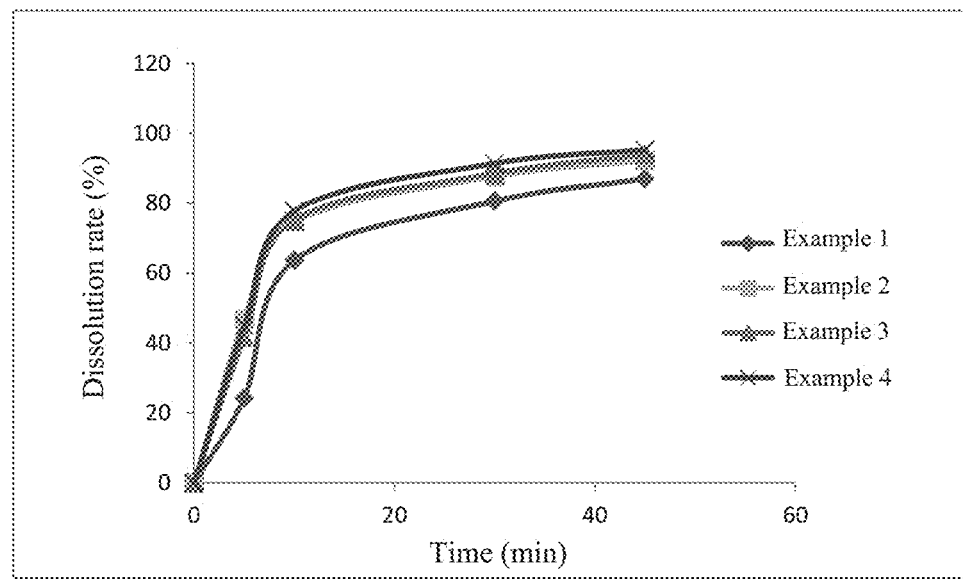
FIG. 1 shows the dissolution profile of the tablets of Example 1 in pH 6.8 phosphate buffer.

The dissolution rates of the tablets of Examples 1-4 were determined according to the second method (paddle method) of the dissolution rate test described in general rule 0931 of volume IV of Chinese Pharmacopoeia 2015 Edition. The dissolution test was carried out using 1000 ml of pH 6.8 phosphate buffer as a dissolution medium at 37±0.5° C. and at the paddle speed of 50 rpm. The results show that the dissolution of compound A in Experimental example 1 is slow and incomplete; the dissolution of compound A in Experimental examples 2 and 3 is rapid but incomplete; and the dissolution of compound A in Example 4 is rapid and complete. The dissolution data are shown in Table 2 below, and the dissolution profile is shown in FIG. 1.

TABLE 2

| Time (min) | Dissolution rate (%) | | | |
|---|---|---|---|---|
| | 1 | 2 | 3 | 4 |
| 5 | 24.4 | 46.7 | 41.7 | 44.8 |
| 10 | 63.7 | 74.7 | 75.2 | 77.8 |
| 30 | 80.6 | 87.7 | 88.5 | 91.4 |
| 45 | 87.0 | 92.2 | 93.9 | 95.3 |

Example 2

According to the ratios shown in Table 3, 2-((2-fluoro-4-iodophenyl)amino)-1-methyl-4-((6-methylpyridin-3-yl)oxy)-6-oxo-1,6-di hydropyridine-3-carboxamide p-toluenesulfonate (hereinafter referred to as compound A), mannitol, microcrystalline cellulose and croscarmellose sodium were wet-granulated by a high speed shear granulator, using a 4% aqueous solution of hydroxypropyl methylcellulose as a wetting agent. The wet and soft material was wet-milled and dried, and then the dry granules (water content less than 3%) were dry-milled. A prescription amount of magnesium stearate was added, and mixed well with the granules. The resulting total mixed granules were compressed into tablets.

TABLE 3

| Ingredient | Experimental examples (mg/tablet) | | | |
|---|---|---|---|---|
| | 4 | 5 | 6 | 7 |
| Compound A | 2.696 | 1.348 | 0.674 | 0.168 |
| Mannitol | 59 | 60.3 | 61.0 | 61.5 |
| Microcrystalline cellulose pH101 | 30 | 30 | 30 | 30 |
| Croscarmellose sodium | 5 | 5 | 5 | 5 |
| Hydroxypropyl methylcellulose E5 (4%) | 2.4 | 2.4 | 2.4 | 2.4 |
| Magnesium stearate | 1.0 | 1.0 | 1.0 | 1.0 |
| Total | 100 | 100 | 100 | 100 |

Figure 2:
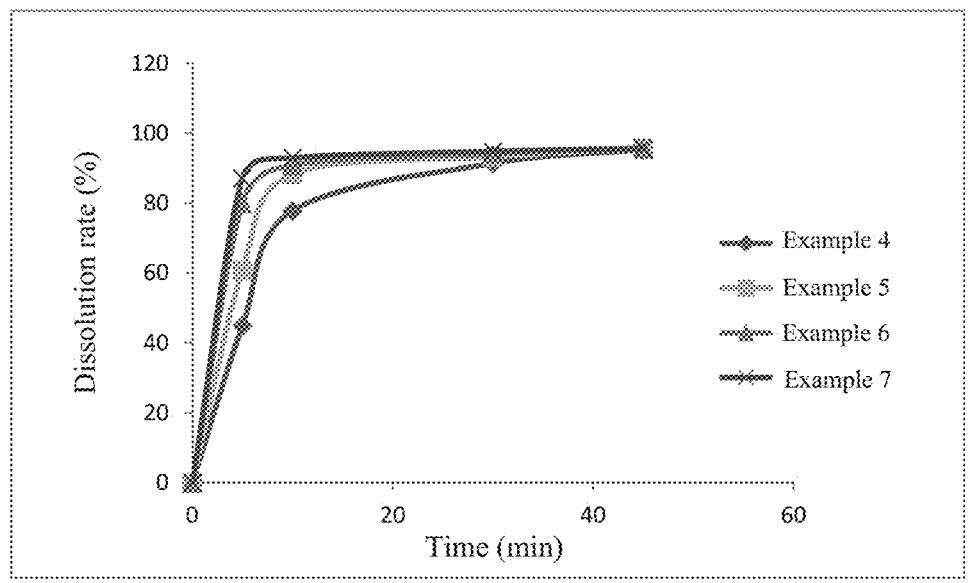
FIG. 2 shows the dissolution profile of the tablets of Example 2 in pH 6.8 phosphate buffer.

The dissolution rates of the tablets of Experimental examples 4-7 were determined according to the second method (paddle method) of the dissolution rate test described in general rule 0931 of volume IV of Chinese Pharmacopoeia 2015 Edition. The dissolution test was carried out using 1000 ml of pH 6.8 phosphate buffer as a dissolution medium at 37±0.5° C. and at the paddle speed of 50 rpm. The results show that the dissolution in Experimental examples 4-7 is complete. The dissolution data are shown in Table 4 below, and the dissolution profile is shown in FIG. 2.

TABLE 4

| Time (min) | Dissolution rate (%) | | | |
|---|---|---|---|---|
| | 4 | 5 | 6 | 7 |
| 5 | 44.8 | 60.8 | 79.9 | 87.0 |
| 10 | 77.8 | 88.2 | 90.9 | 92.9 |
| 30 | 91.4 | 93.2 | 94.1 | 94.8 |
| 45 | 95.3 | 95.8 | 95.5 | 95.7 |

Example 3

2-((2-Fluoro-4-iodophenyl)amino)-1-methyl-4-((6-methylpyridin-3-yl)oxy)-6-oxo-1,6-dihydropyridine-3-carboxamide p-toluenesulfonate (hereinafter referred to as compound A) was screened by an 80 mesh sieve, and micronized by a Mcone jet mill (micronizing pressure: 4 bar, sample introduction pressure: 6 bar), respectively. The particle size was measured directly with a Malvern laser particle size analyzer (Mastersizer 2000). The results are shown in Table 5 below.

TABLE 5

| Treatment of the raw material | Particle size d (0.5) of the raw material | Particle size d (0.9) of the raw material |
|---|---|---|
| Screening by an 80 mesh sieve | 4.940 | 14.148 |
| Micronization by a jet mill | 2.587 | 5.494 |

Example 4

According to the ratio of Experimental example 4 shown in Table 1, 2-((2-fluoro-4-iodophenyl)amino)-1-methyl-4-((6-methylpyridin-3-yl)oxy)-6-oxo-1,6-di hydropyridine-3-carboxamide p-toluenesulfonate (hereinafter referred to as compound A) treated according to Example 3, mannitol, microcrystalline cellulose and croscarmellose sodium were wet-granulated by a high speed shear granulator, using a 4% aqueous solution of hydroxypropyl methylcellulose as a wetting agent. The wet and soft material was wet-milled and dried, and then the dry granules (water content less than 3%) were dry-milled. A prescription amount of magnesium stearate was added, and mixed well with the granules. The resulting total mixed granules were compressed into tablets.

Figure 3:
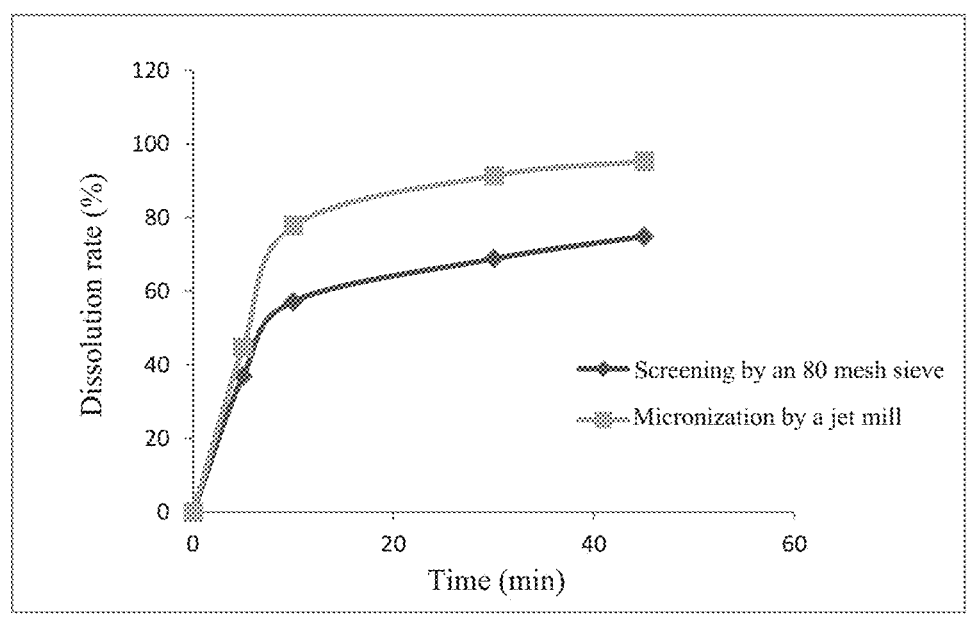
FIG. 3 shows the dissolution profile of the tablets of Example 4 in pH 6.8 phosphate buffer.

The dissolution rates of the tablets of Example 4 were determined according to the second method (paddle method) of the dissolution rate test described in general rule 0931 of volume IV of Chinese Pharmacopoeia 2015 Edition. The dissolution test was carried out using 1000 ml of pH 6.8 phosphate buffer as a dissolution medium at 37±0.5° C. and at the paddle speed of 50 rpm. The results show that the particle size of the raw material micronized by a jet mill is less than that of the raw material screened by an 80 mesh sieve, and is less than 10 μm; the dissolution of the sample prepared from the raw material screened by an 80 mesh sieve is incomplete; and the dissolution rate of the sample prepared from the raw material micronized by a jet mill is obviously more rapid than that of the sample prepared from the raw material screened by an 80 mesh sieve, and the dissolution is complete. The dissolution data are shown in Table 6 below, and the dissolution profile is shown in FIG. 3.

TABLE 6

| Treatment of the raw material | Dissolution rate (%) | | | |
|---|---|---|---|---|
| | 5 min | 15 min | 30 min | 45 min |
| Screening by an 80 mesh sieve | 37.0 | 57.2 | 68.8 | 74.9 |
| Micronization by a jet mill | 44.8 | 77.8 | 91.4 | 95.3 |

Example 5

According to the ratios shown in Table 1, 2-((2-fluoro-4-iodophenyl)amino)-1-methyl-4-((6-methylpyridin-3-yl)oxy)-6-oxo-1,6-di hydropyridine-3-carboxamide p-toluenesulfonate (hereinafter referred to as compound A), mannitol, microcrystalline cellulose and croscarmellose sodium were wet-granulated by a high speed shear granulator, using a 3% aqueous solution of hydroxypropyl methylcellulose as a wetting agent. The wet and soft material was wet-milled and dried, and then the dry granules (water content less than 3%) were dry-milled. A prescription amount of magnesium stearate was added, and mixed well with the granules. The resulting total mixed granules were compressed into tablets.

TABLE 7

| Ingredient | Experimental examples (mg/tablet) | | |
|---|---|---|---|
| | 2 | 5 | 3 |
| Compound A | 2.7 | 2.7 | 2.7 |
| Mannitol | 70 | 65 | 60 |
| Microcrystalline cellulose pH101 | 20 | 35 | 30 |
| Croscarmellose sodium | 5 | 5 | 5 |
| Hydroxypropyl methylcellulose E5 (3%) | 1.7 | 1.8 | 2 |
| Magnesium stearate | 1.0 | 1.0 | 1.0 |
| Total | 100.4 | 100.5 | 100.7 |

In Experimental example 2, the amount of microcrystalline cellulose was small, and the punch jamming phenomenon occurred during the preparation of tablets. In Experimental example 5, the amount of microcrystalline cellulose was increased, and the punch jamming phenomenon was improved. In Experimental example 3, the punch jamming phenomenon did not occur at all.

What is claimed is:
1. An oral solid pharmaceutical composition, comprising 2-((2-fluoro-4-iodophenyl)amino)-1-methyl-4-((6-methylpyridin-3-yl)oxy)-6-oxo-1,6-dihydropyridine-3-carboxamide or a pharmaceutically acceptable salt thereof, and hydroxypropyl methylcellulose, wherein the pharmaceutical composition has a content of 0.01-10% by weight of 2-((2-fluoro-4-iodophenyl)amino)-1-methyl-4-((6-methylpyridin-3-yl)oxy)-6-oxo-1,6-dihydropyridine-3-carboxamide or the pharmaceutically acceptable salt thereof, relative to a weight of the pharmaceutical composition, the hydroxypropyl methylcellulose is present in an amount of 1.5-3% by weight, relative to the weight of the pharmaceutical composition, and the pharmaceutical composition has a dissolution rate in 30 minutes greater than or equal to 85%, according to the dissolution test carried out using pH 6.8 phosphate buffer.

2. The pharmaceutical composition according to claim 1, wherein the pharmaceutical composition further comprises a filler, and the filler is at least one selected from the group consisting of mannitol, lactose, microcrystalline cellulose, pregelatinized starch and calcium hydrophosphate.

3. The pharmaceutical composition according to claim 2, wherein the filler is present in an amount of 30-95% by weight, relative to a weight of the pharmaceutical composition.

4. The pharmaceutical composition according to claim 1, wherein the pharmaceutical composition further comprises at least one pharmaceutical auxiliary material selected from the group consisting of a disintegrant, a glidant, a lubricant and a coating agent.

5. The pharmaceutical composition according to claim 4, wherein the disintegrant is at least one selected from the group consisting of carboxymethyl cellulose sodium, sodium carboxymethyl starch, crospovidone and low-substituted hydroxypropyl cellulose, and the disintegrant is present in an amount of 2-15% by weight, relative to a weight of the pharmaceutical composition.

6. The pharmaceutical composition according to claim 4, wherein the lubricant is at least one selected from the group consisting of magnesium stearate, stearic acid, palmitic acid, calcium stearate, talc, carnauba wax and sodium stearyl fumarate, and the lubricant is present in an amount of 0.1-5% by weight, relative to a weight of the pharmaceutical composition.

7. The pharmaceutical composition according to claim 1, wherein the pharmaceutically acceptable salt is p-toluenesulfonate.

8. An oral solid pharmaceutical composition, comprising:
   a) 0.1-5% by weight of 2-((2-fluoro-4-iodophenyl)amino)-1-methyl-4-((6-methylpyridin-3-yl)oxy)-6-oxo-1,6-dihydropyridine-3-carboxamide or a pharmaceutically acceptable salt thereof,
   b) 2-15% by weight of a disintegrant, wherein the disintegrant is at least one selected from the group consisting of croscarmellose sodium, sodium carboxymethyl starch, crospovidone and low-substituted hydroxypropyl cellulose,
   c) 50-94% by weight of a filler, wherein the filler is at least one selected from the group consisting of mannitol and microcrystalline cellulose,
   d) 1.5-3% by weight of hydroxypropyl methylcellulose, and
   e) 0.5-3% by weight of a lubricant, wherein the lubricant is at least one selected from the group consisting of magnesium stearate, stearic acid, palmitic acid, calcium stearate, talc, carnauba wax and sodium stearyl fumarate, wherein the pharmaceutical composition has a dissolution rate in 30 minutes greater than or equal to 85%, according to the dissolution test carried out using pH 6.8 phosphate buffer.

9. The pharmaceutical composition according to claim 8, wherein the filler consists of mannitol and microcrystalline cellulose.

10. An oral solid pharmaceutical composition, comprising 2-((2-fluoro-4-iodophenyl)amino)-1-methyl-4-((6-methylpyridin-3-yl)oxy)-6-oxo-1,6-dihydropyridine-3-carboxamide or a pharmaceutically acceptable salt thereof, hydroxypropyl methylcellulose, mannitol and microcrystalline cellulose, wherein a weight ratio of the mannitol to the microcrystalline cellulose is 1.5:1-10:1, wherein the hydroxypropyl methylcellulose is present in an amount of 1.5-3% by weight, relative to the weight of the pharmaceutical composition, and the pharmaceutical composition has a dissolution rate in 30 minutes greater than or equal to 85%, according to the dissolution test carried out using pH 6.8 phosphate buffer.

11. The pharmaceutical composition according to claim 10, wherein the pharmaceutical composition has a content of 0.01-10% by weight of 2-((2-fluoro-4-iodophenyl)amino)-1-methyl-4-((6-methylpyridin-3-yl)oxy)-6-oxo-1,6-dihydropyridine-3-carboxamide or the pharmaceutically acceptable salt thereof; and a total amount of the mannitol and the microcrystalline cellulose is 30-95% by weight, relative to a weight of the pharmaceutical composition.

12. The pharmaceutical composition according to claim 1, wherein the dissolution rate of the pharmaceutical composition is determined according to the second method (paddle method) of dissolution rate test described in general rule 0931 of volume IV of Chinese Pharmacopoeia 2015 Edition, and the dissolution rate in 45 minutes is greater than or equal to 90%.

13. A method for preparing the pharmaceutical composition according to claim 1, comprising: 1) mixing 2-((2-fluoro-4-iodophenyl)amino)-1-methyl-4-((6-methylpyridin-3-yl)oxy)-6-oxo-1,6-dihydropyridine-3-carboxamide or a pharmaceutically acceptable salt thereof with a disintegrant and optionally at least one pharmaceutical auxiliary material selected from the group consisting of a filler, a binder, a lubricant and a glidant to obtain a mixture, 2) granulating the mixture obtained in 1) to obtain granules, and tableting the granules or filling the granules into capsules, or directly tableting the mixture obtained in 1), or directly filling the mixture obtained in 1) into capsules.

14. The pharmaceutical composition according to claim 2, wherein the filler consists of mannitol and microcrystalline cellulose, and a weight ratio of the mannitol to the microcrystalline cellulose is 1.5:1 to 10:1.

15. The pharmaceutical composition according to claim 9, wherein a weight ratio of the mannitol to the microcrystalline cellulose is 1.5:1 to 10:1.

16. The pharmaceutical composition according to claim 8, wherein the dissolution rate of the pharmaceutical composition is determined according to the second method (paddle method) of dissolution rate test described in general rule 0931 of volume IV of Chinese Pharmacopoeia 2015 Edition, and the dissolution rate of 2-((2-fluoro-4-iodophenyl)amino)-1-methyl-4-((6-methylpyridin-3-yl)oxy)-6-oxo-1,6-dihydropyridine-3-carboxamide or the pharmaceutically acceptable salt thereof in 45 minutes is greater than or equal to 90%.

17. The pharmaceutical composition according to claim 10, wherein the dissolution rate of the pharmaceutical composition is determined according to the second method (paddle method) of dissolution rate test described in general rule 0931 of volume IV of Chinese Pharmacopoeia 2015 Edition, and the dissolution rate of 2-((2-fluoro-4-iodophenyl)amino)-1-methyl-4-((6-methylpyridin-3-yl)oxy)-6-oxo-1,6-dihydropyridine-3-carboxamide or the pharmaceutically acceptable salt thereof in 45 minutes is greater than or equal to 90%.

* * * * *